United States Patent
Takashima et al.

(10) Patent No.: US 7,126,037 B2
(45) Date of Patent: Oct. 24, 2006

(54) BUTENE OLIGOMER DERIVATIVES HAVING TERMINAL 1,4-BUTANEDIOL FUNCTIONAL GROUPS

(75) Inventors: Tsutomu Takashima, Kawasaki (JP); Koji Fujimura, Kisarazu (JP); Yuichi Tokumoto, Chigasaki (JP)

(73) Assignee: Nippon Petrochemicals Co., Lt., Tokyo (JP)

( * ) Notice: Subject to any disclaimer, the term of this patent is extended or adjusted under 35 U.S.C. 154(b) by 214 days.

(21) Appl. No.: 10/204,232

(22) PCT Filed: Dec. 19, 2000

(86) PCT No.: PCT/JP00/08996

§ 371 (c)(1),
(2), (4) Date: Aug. 29, 2003

(87) PCT Pub. No.: WO02/50139

PCT Pub. Date: Jun. 27, 2002

(65) Prior Publication Data

US 2004/0034184 A1 Feb. 19, 2004

(51) Int. Cl.
*C07C 2/30* (2006.01)
(52) U.S. Cl. .............. 585/511; 585/512; 585/520; 585/521; 585/522; 585/531; 585/532
(58) Field of Classification Search ............. 585/511, 585/512, 520, 522, 531, 532
See application file for complete search history.

(56) References Cited

U.S. PATENT DOCUMENTS

| 3,786,116 A | 1/1974 | Milkovich et al. |
| 4,146,590 A | 3/1979 | Yamamoto et al. |
| 4,152,499 A | 5/1979 | Boerzel et al. |
| 4,548,724 A * | 10/1985 | Karol et al. ............ 508/291 |
| 4,808,664 A | 2/1989 | Saam |
| 5,008,338 A | 4/1991 | Riddick et al. |
| 5,646,215 A | 7/1997 | Lee |

FOREIGN PATENT DOCUMENTS

| DE | 25 01 123 | 7/1976 |
| GB | 834347 | 5/1960 |
| JP | 55-84302 | 6/1980 |
| JP | H08-291183 | 11/1996 |
| JP | 9-249717 | 9/1997 |
| JP | 2696076 | 9/1997 |
| JP | H10-306128 | 11/1998 |

* cited by examiner

*Primary Examiner*—Robert D. Harlan
(74) *Attorney, Agent, or Firm*—Scully, Scott, Murphy & Presser, P.C.

(57) ABSTRACT

Butene oligomer derivatives having tert-butyl groups as one of the terminal groups, having a repeating unit of the main hydrocarbon chain consisting of 80% by mole or more of $-CH_2C(CH_3)_2-$, and carrying the other terminal group consisting of 60% by mole or more of 1,4-butanediol type functional groups. These derivatives are useful as macromonomers which can be subjected to polycondensation, polyaddition, etc.

8 Claims, 6 Drawing Sheets

BUTENE OLIGOMER DERIVATIVES HAVING TERMINAL 1,4-BUTANEDIOL FUNCTIONAL GROUPS

TECHNICAL FIELD

The present invention relates to new butene oligomer derivatives having terminal 1,4-butanediol functional groups, as macromonomers that can be used for polycondensation and polyaddition.

BACKGROUND ART

The macromonomer means a compound that can be regarded as a high molecular weight monomer (usually several hundreds to ten thousands in molecular weight) that contains a polymerizable functional group on one terminal end of the molecule. It was first proposed by Milkovich et al. of U.S.A. in 1972 (cf. U.S. Pat. No. 3,786,116 (1976) or ACS Polym. Prepr., 21, 40 (1980), etc.)

In graft copolymerization through the conventional chain transfer reaction, a branch-forming monomer is subjected to polymerization in the presence of main carbon chain polymers. Therefore, the obtained graft polymer is uneven in the lengths and distribution of the branches. However, according to a newly proposed macromonomer method, a macromonomer can be produced by previously controlling properties such as molecular weight and its distribution, stereoregularity, hydrophobic property and hydrophilic property. Such a macromonomer is used in polycondensation or polyaddition to produce a graft polymer, which is excellent as a method for designing the graft polymer molecule having a regulated molecular structure.

An example of the method for creating a new material by utilizing the macromonomer method is disclosed in the literature of "Chemistry and Industry of Macromonomer" (Yuya Yamashita, (1989), published by I. P. C.), in which a wide variety of macromonomers are proposed.

Meanwhile, several attempts to utilize butene oligomer derivatives as macromonomers have been done. However, in most butene oligomers, the main chain components are composed of isobutylene skeleton and they have functional groups at both α-terminals and ω-terminals. For example, J. P. Kennedy et al. disclose the production of a butene oligomer derivative having an isobutylene main chain and epoxy functional groups at both terminal ends, in a report of "Journal of Polymer Science", Polymer Chemical Edition, vol. 20, p. 2809–2817 (1982).

However, it is apparent that the butene oligomer derivative like this having functional groups at both terminals is substantially different in molecular structure from the butene oligomer derivative having functional group on one side end of molecule according to the present invention.

As the butene oligomer which can be used as base polymer for developing butene oligomer derivatives, what is called "less reactive butene oligomer" has hitherto been produced using a catalyst of aluminum chloride or the like. In recent years, however, what is called "highly reactive butene oligomer" has been produced by changing its structure, especially the type of bonding olefin, by using various catalysts. This butene oligomer contains a large quantity of terminal vinylidene structure.

For example, in U.S. Pat. No. 4,152,499, a method for producing highly reactive butene oligomer is disclosed. Furthermore, it is also disclosed that a butene oligomer derivative having terminal group of succinic acid (hereinafter referred to as "succinic acid derivative") can be produced at a high yield by reacting the butene oligomer with maleic anhydride.

As new derivatives utilizing the chemical reactivity of the highly reactive butene oligomer, there are several reports as well as the above-mentioned one on succinic acid derivative.

For example, there are carbonyl derivative in Japanese Patent No. 2,908,557; silyl derivative in Japanese Laid-Open Patent Publication No. H08-291,183; and oxo derivative and its modified compounds of monoamine derivatives in Japanese Patent No. 2,696,076.

As mentioned above, butene oligomer derivative as macromonomer that is capable of causing polycondensation/polyaddition at one side of terminals has never been disclosed.

It is, therefore, the object of the present invention to provide novel butene oligomer derivatives, as macromonomers, having functional groups of 1,4-butanediol at terminal ends, which macromonomer can be subjected to polycondensation and polyaddition.

DISCLOSURE OF INVENTION

That is, a first aspect of the present invention relates to butene oligomer derivatives having the structure as defined by the following conditions of (1) to (3) (hereinafter referred to as "saturated diol derivatives"), (1) terminal groups on one side of molecules are tert-butyl groups, (2) 80% by mole or more of the repeating structural units of hydrocarbon main chains are represented by the following formula [1], and (3) 60% by mole or more of the other side terminal groups have saturated 1,4-butanediol type functional groups as represented by the following formula [2].

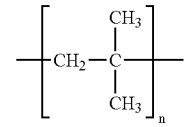

wherein n is an integer of 0 or more, preferably 5 or more, more preferably 16 or more, but 200 or less.

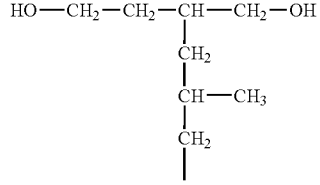

A second aspect of the present invention relates to butene oligomer derivatives having the following structures of (1) to (3) (hereinafter referred to as "unsaturated diol derivatives"), (1) terminal groups on one side are tert-butyl groups, (2) 80% by mole or more of the repeating structural units of hydrocarbon main chains are represented by the following formula [1], and (3) 60% by mole or more of the other side terminal groups have 1,4-butanediol type functional groups, with unsaturated olefinic structures, as represented by the following formula [3] or [4].

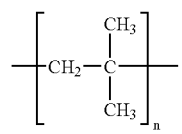
[1]

wherein n is an integer of 0 or more, preferably 5 or more, more preferably 16 or more, but 200 or less.

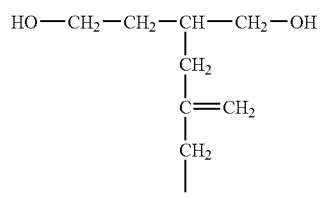
[3]

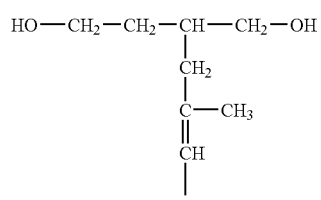
[4]

In the following, the present invention will be described in more detail.

The saturated or unsaturated 1,4-butanediol derivatives of the present invention can be produced step by step as follows, from butene oligomer having specific structure and through succinic acid derivative.

In the first place, a highly reactive butene oligomer having the following specific structure is used as a starting material to produce succinic acid derivative.

(1) terminal groups on one side are tert-butyl groups, (2) 80% by mole or more of hydrocarbon main chains is composed of the repeating structural units as represented by the following formula [1], and (3) 60% by mole or more of terminal groups on the other side have the terminal vinylidene groups as represented by the following formula [5].

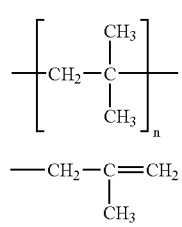
[1]

[5]

wherein n is an integer of 0 or more preferably 5 or more, more preferably 16 or more, but 200 or less.

The above highly reactive butene oligomers having specific structure can be produced by polymerizing isobutylene singly or carrying out appropriate cation polymerization of isobutylene with olefin such as butene-1, butene-2 or a mixture of them. In the reaction process, $BF_3$ catalyst can be used as described in examples of the foregoing U.S. Pat. No. 4,152,499; and it is possible to refer to the method as disclosed in Japanese Laid-Open Patent Publication No. H10-306128 that was developed by the present inventors.

Next, in order to produce a succinic acid derivative using the above highly reactive butene oligomer, it is possible to add maleic anhydride to highly reactive butene oligomer by heating them without using any catalyst, as typically disclosed in the foregoing U.S. Pat. No. 4,152,499.

The above addition of maleic anhydride proceeds according to the mechanism of Ene-reaction, which has been disclosed in M. Tessier et al., European Polymer Journal, vol. 20, no. 3, p. 269–280 (1984). Furthermore, the structure of the product is specified as follows.

When maleic anhydride is added to olefin moiety of the terminal vinylidene group of the compound of the formula [5] through Ene-reaction, the terminal group is converted into a succinic acid terminal group having unsaturated olefin moiety, as represented by the following formula [6] or [7].

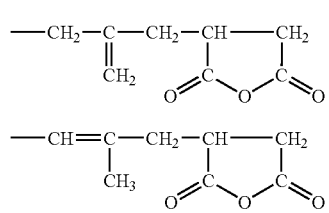

The difference between both the formed compounds depends upon the type of olefin substitution. The terminal group of formula [6] is vinylidene type, and that of formula [7] is 3-substitution type. The ratio of yields of the succinic acid derivative of formula [6] to that of formula [7] vary depending on the producing conditions. Generally, the compound of formula [6] is produced much more.

The thus produced succinic acid derivatives having specific structures can be used as a starting material for producing the saturated or unsaturated diol derivatives of the present invention.

In the following, the method for producing saturated diol derivative of the formula [2] and the method for producing unsaturated diol derivative of the formula [3] or [4], will be described. By the way, it should be noted that all of these compounds according to the present invention are novel substances, which have never been disclosed in any prior art reference.

(Production of Unsaturated Diol Derivative)

Unsaturated diol derivatives can be synthesized by using the above succinic acid derivative as a starting material and lithium aluminum hydride ($LiAlH_4$) as a reducing reagent, and thereby reducing carbonyl groups in succinic acid terminal groups into methylene groups.

The above reducing method using $LiAlH_4$ is well known in the art of organic chemistry and polymer chemistry. Theoretically, 1 mole of $LiAlH_4$ has an ability to reduce 4 moles of carbonyl groups. Because 1 mole of the above succinic acid derivative contains at least 2 moles of carbonyl groups, 0.5 mole or more of $LiAlH_4$ is necessary in order to produce unsaturated diol derivative from 1 mole of succinic acid derivative. In practical production process, it is preferable to react 1 mole of succinic acid derivative with a large excess of 5 moles or more of $LiAlH_4$ because the reaction time can be reduced.

In the reduction with $LiAlH_4$, when carbonyl group and olefinic double bond coexist in one molecule, it is also well known that only carbonyl group is reduced selectively.

In a typical process for reducing succinic acid derivative using $LiAlH_4$ according to the present invention, the reaction can be done with stirring in which the succinic acid derivative diluted with a reaction solvent is dropped into a solution of a fixed quantity of $LiAlH_4$ in the reaction solvent.

The reaction conditions such as temperature and duration are not particularly limited. For example, the reaction temperature is in the range of 0 to 200° C., the refluxing temperature of reaction solvent is preferably adopted. There is no difficulty if the time length of reaction may be 5 minutes or longer.

As reaction solvents used for the reduction, compounds which are inactive to $LiAlH_4$ are used. In other words, the compounds that do not contain carbonyl group can be used, which are exemplified by aromatic hydrocarbon solvents such as benzene, toluene and xylene; aliphatic hydrocarbon solvents such as isooctane; and ether solvents such as tetrahydrofuran (THF) and diethyl ether. More preferably, the reduction is carried out using a reactant itself as a solvent without using any other solvent.

When the succinic acid derivative having a high molecular weight is used as a feed material, the efficiency of contact with $LiAlH_4$ in the interface of reaction varies depending on the viscosity of reactants. Furthermore, the unsaturated diol derivatives produced by reduction have viscosity similar to that of feed material. Therefore, it is preferable to dilute both the feed material and $LiAlH_4$ with the above solvents.

After the above reduction process, after-treatment is carried out according to conventional method. In this case, it is necessary to deactivate and remove the unreacted $LiAlH_4$. As the method of deactivation, water or a compound containing carbonyl group such as acetone is added dropwise. Subsequently, in order to remove inorganic residues that are liberated in the deactivation, the process is followed by neutralization and water washing using water or saturated saline solution. Furthermore, the organic layer obtained through this neutralization and water washing is dried with a desiccating agent such as anhydrous sodium sulfate, then the solution is concentrated by distillation or the like to obtain an intended compound.

In the product obtained as above, carbonyl groups in the succinic acid terminal group as represented by the above formula [6] or [7] are reduced. The terminal group of the formula [6] is converted into the structure as represented by the formula [3], and the terminal group of the formula [7] is converted into the structure as represented by the formula [4], each of which is unsaturated diol. In other words, olefinic double bonds in the succinic acid terminal groups as represented by the above formula [6] and [7] are not subjected to isomerization. The terminal groups are converted into the unsaturated diol terminal groups as represented by the formula [3] and [4], respectively, which retain the same combination structures as before.

The thus produced unsaturated diol derivative is a substance that is stable under ordinary temperature and pressure. Accordingly, in order to refine the obtained unsaturated diol derivative up to still a higher purity, the isolation and recovery can be accomplished without difficulty by using the conventional method of separation such as silica gel chromatography.

(Production of Saturated Diol Derivative)

Saturated diol derivatives can be synthesized by subjecting olefin moiety in the unsaturated diol derivatives to catalytic reduction with an appropriate hydrogenating catalyst.

Catalytic reduction of olefin moiety is practiced widely in chemical industries. In the specific method according to the present invention, the hydrogen pressure is from atmospheric pressure to 10 MPa, preferably 2 MPa or lower, and the reaction temperature is in the range of 0 to 200° C., preferably 100° C. or lower.

By subjecting the unsaturated diol derivatives diluted with an appropriate solvent to catalytic reduction using a hydrogenating catalyst, it is possible to reduce the olefin moieties that are present in the respective unsaturated diol derivatives, thereby converting them, into saturated diol derivatives in high yield. Though the duration of reaction is not particularly limited, it is usually about 1 to 3 hours.

The catalytic system may be either in homogeneous or in heterogeneous, and the kind of catalyst is not particularly limited. However, a heterogeneous catalyst system of noble metal is preferable in the reduction of olefin moieties according to the present invention, from the viewpoint of separation of products. In other words, catalysts of noble metals such as Pd, Pt and Ru can be used, and these noble metals can be supported on inert carriers such as alumina, silica and activated carbon. Because only a small quantity of the above catalyst can produce its catalytic effect, the use quantity of the catalyst can be small. For example, 0.01 to 50% by mole of catalyst relative to an unsaturated diol derivative is satisfactory.

As the reaction solvents usable in this reaction, those which can dissolve a feed material of unsaturated diol derivative and which are inactive in the reaction, can be used. They are exemplified by aliphatic hydrocarbon solvents such as hexane and isooctane; and ether solvents such as tetrahydrofuran (THF). More preferably, the reduction is carried out using a reactant itself as a solvent without using any other solvent.

When an unsaturated diol derivative having a large molecular weight is especially used as a starting material, the efficiency of contact with catalysts in the interface of reaction varies depending upon liquid viscosity of reaction system. Furthermore, the saturated diol derivative produced by reduction have similar viscosity as that of the starting material. Therefore, it is preferable to dilute the starting materials themselves with the above solvents.

After the above catalytic reduction, a residual catalyst is removed by a conventional procedure such as filtration. When a reaction solvent is used, the reacted solution separated from the catalyst is treated with appropriate means of separation and recovery such as concentration and drying to obtain an intended saturated diol derivative.

In the product obtained as above, the olefin moiety in the unsaturated diol derivative having the terminal group as represented by the foregoing formula [3] or [4] is reduced, and each compound is converted into the saturated diol derivative as represented by the formula [2].

The thus produced saturated diol derivative is stable under ordinary temperature and pressure. Accordingly, in order to refine the produced saturated diol derivative up to still higher purity, isolation and recovery can be accomplished without difficulty by a conventional method of separation such as silica gel chromatography.

The saturated and unsaturated diol derivatives obtained in the present invention are 1,4-butanediol type macromonomers having a reactive functional group of primary diol at the terminal end of molecule. The 1,4-butanediol is generally known as being chemically reactive, and it reacts easily with functional groups such as carboxyl group, isocyanate group and acrylic group.

The butene oligomer having the terminal group of 1,4-butanediol type according to the present invention is also known to be chemically reactive, that is compared favorably with the above-mentioned 1,4-butanediol. So that, it can react easily with functional groups such as carboxyl group, isocyanate group and acrylic group in the same way as the above.

In recent years, the demand for polybutylene terephthalate (PBT) as engineering plastics has been rapidly increasing, which polymer is a polycondensate of polyester that is produced by using a monomer of 1,4-butanediol. Because the butene oligomer derivative of the present invention has a chemical reactivity which stands comparison with that of 1,4-butanediol, it is possible by using the above derivative to obtain a novel polycondensate of polyester having new properties that could not be attained by using 1,4-butanediol. Furthermore, the butene oligomer derivative according to the present invention can be used for polyaddition, so that it is possible to provide a new polyaddition product of polyurethane.

As described above, the saturated or unsaturated diol derivative of the present invention provides polyesters through polycondensation with organic molecules having dicarboxyl or diester functional group, while provides polyurethane through polyaddition with organic molecules having diisocyanate functional group. Moreover, if the diol derivative is converted into acrylic derivative by modification with acrylic group, the copolymerization with other ethylenic monomers is made possible.

The saturated or unsaturated diol derivative according to the present invention can also be used as plasticizers for various kinds of plastics such as polyethylene, polypropylene, polystyrene, polyvinyl chloride and polyamide. That is, when these plastics have functional groups such as carboxyl group or isocyanate group that can react with the derivatives of the present invention, they react with the functional diol groups in the derivatives of the present invention as a reactive plasticizing agent.

Furthermore, because the unsaturated diol derivative of the present invention has an olefin moiety in the terminal group, it can be used as a third component capable of hardening sulfur-curable rubber. The sulfur-curable rubber is exemplified by those produced from dienes, preferably from conjugated aliphatic 1,3-diene having carbon atoms of 4 to 8 such as butadiene and isoprene. More particularly, rubbers are exemplified by natural rubber; polybutadiene-1,3; poly-isoprene; poly-2,3-dimetyl-butadiene-1,3; and poly-2-chloro-butadiene-1,3. As other useful rubbers, there are polymers of 1,3-dienes; and the copolymers or terpolymers consisting of these dienes and at least one copolymerizable monomer, such as isobutylene, styrene, acrylonitrile, methyl acrylate, methyl methacrylate and 4-vinylpyridine.

As described above, the butene oligomer derivatives of the present invention can be used as macromonomers for synthesizing a new polymer in the above-mentioned polycondensation and polyaddition, as plasticizers for various kinds of plastics, and as a third component capable of hardening sulfur-curable rubbers. It is thus possible to create functional materials having improved properties that have never been obtained by highly reactive butene oligomer singly or 1,4-butanediol singly.

In order to obtain satisfactory results in the use of the above derivatives of the present invention, it is essential that butene oligomer as a starting material has a fixed molecular weight and has a regular molecular skeletal structure of the repeating units as represented by the above formula [1].

The molecular weight of butene oligomer is determined by measurement with mass spectrometry (MS) or gel permeation chromatography (GPC). When butene oligomer of the present invention has a high molecular weight, the measurement is carried out with GPC, and the degree of dispersion (Mw/Mn) is in the range of 1.0 to 2.5. Because the range of molecular weight distribution is narrow like this, the butene oligomer can be used as a macromonomer having constant properties.

The molecular skeleton of butene oligomer was determined according to the method described in the prior patent application by the present inventors (Japanese Laid-Open Patent Publication No. H10-306128). That is, the determination of specific molecular skeletons was carried out based on the result of measurements with HSQC method and INADEQUATE method, which examine the carbon-hydrogen combination and carbon-carbon combination with the measurement of nuclear magnetic resonance (NMR).

In HSQC method, taking the chart of $^1$H-NMR as abscissa and the chart of $^{13}$C-NMR as ordinate, the point corresponding to the crossing coordinates of a peak of $^1$H-NMR and a peak of $^{13}$C-NMR indicates that a carbon and a hydrogen corresponding to each peak are connected together. By this method, the connection of carbon-hydrogen in a molecule can be known. Furthermore, in INADEQUATE method, taking the chart of $^{13}$C-NMR as abscissa and the frequency of carbon as ordinate, a straight line is drawn parallel to ordinate from a peak on the abscissa to obtain the position of carbon from the crossing point. When a straight line is drawn from that position parallel to abscissa, the peak of carbon corresponding to a point on the line is the carbon connected with the former carbon. When similar procedures are repeated and the carbons are arranged one after another, the connection between carbon-carbon in a molecule, that is, carbon skeleton can be known.

From the measurements of HSQC method and INADEQUATE method as above, the isobutylene skeleton constituting the butene oligomer of the present invention can be specified, which is represented by the following formula [1]. It was found out that this specific repeating structure constitutes 80% or more of the whole growing chain of repeating structure. One side of terminal groups is usually tert-butyl group.

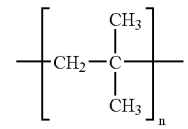

[1]

As being defined in the foregoing passage concerning the butene oligomer molecules obtained according to the present invention, the number (n) in the repeating structural units as represented by the formula [1] is 0 or more, preferably 5 or more, more preferably 16 or more, and its upper limit is 200. The repeating structural units of isobutylene skeleton consists of 80% or more of the whole growing chain of repeating structure, and they are completely straight in molecular structure. Therefore, it is possible to produce specific properties in the utilization of the butene oligomer derivative of the above macromonomer.

BEST METHOD FOR CARRYING OUT THE INVENTION

Figure 1:
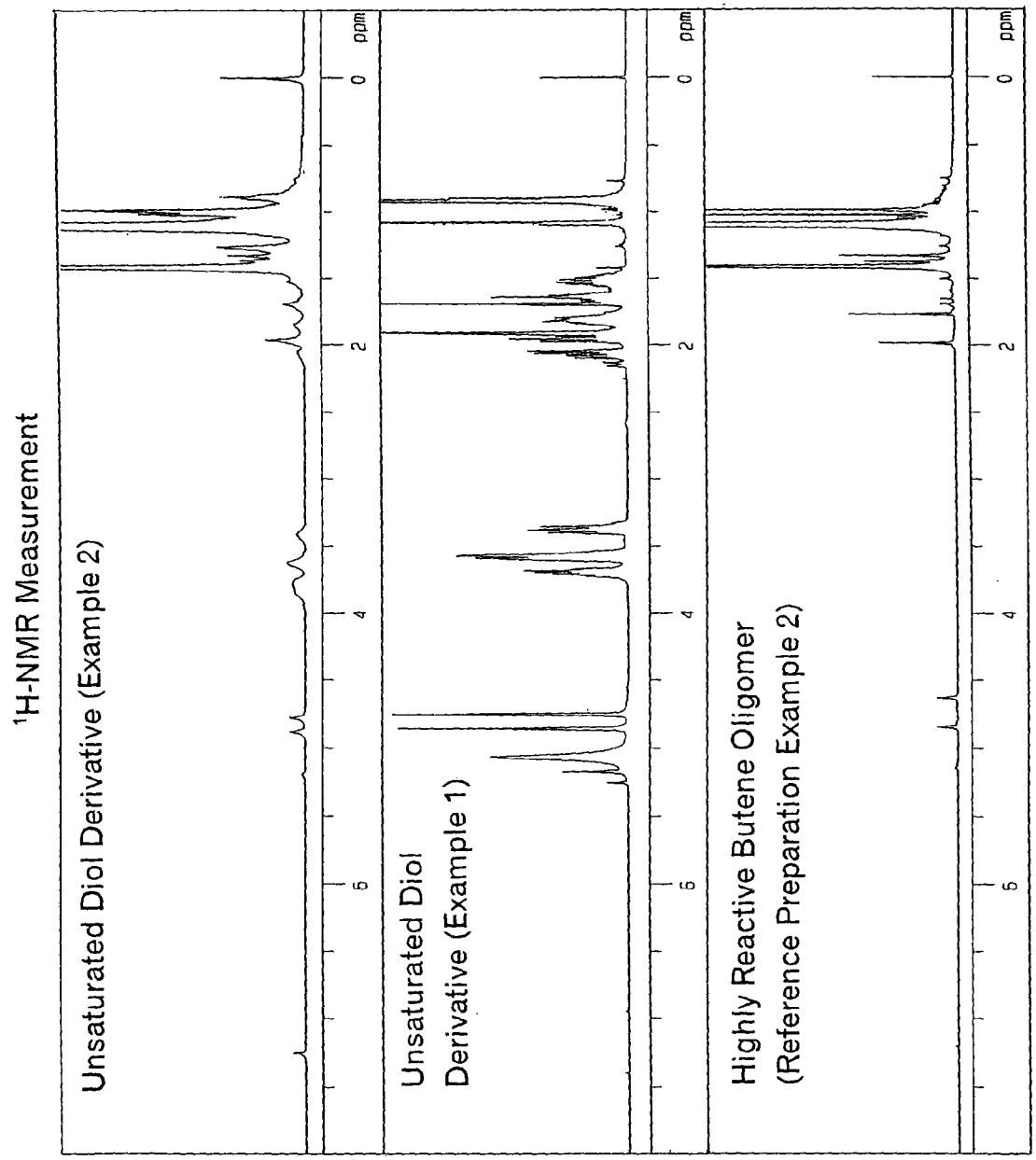
FIG. 1 shows charts of $^1$H-NMR measurement on the unsaturated diol derivatives and a starting material of highly reactive butene oligomer used in the present invention.

In the following, the present invention will be described in more detail with reference to examples.

(Reference Preparation Example)

<Production of Highly Reactive Butene Oligomer>

According to the preparation method disclosed by the present inventors in Japanese Laid-Open Patent Publication No. H10-306128, butene oligomers having Mn=112 (average repeating number n=0), Mn=560 (n=8) and Mn=2300 (n=39), were produced, respectively. Their properties are shown in Table 1.

TABLE 1

| Reference Preparation Example | Mn (*1) | Mw/Mn | Content of Formula [5] (*2) (% by mole) |
|---|---|---|---|
| 1 | 112 | 1.0 | 89 |
| 2 | 560 | 1.4 | 88 |
| 3 | 2300 | 1.5 | 86 |

(*1): The value of Mn in Reference Preparation Example 1 was measured by MS. Those in Reference Preparation Examples 2 and 3 were measured by GPC and expressed in terms of polystyrene.
(*2): Integrated values of peaks of olefins measured by $^{13}$C-NMR (cf. Japanese Laid-Open Patent Publication No. H10-306128)

<Preparation of Succinic Acid Derivative>

In the next step, with reference to a method in examples described in U.S. Pat. No. 4,152,499; three kinds of butene oligomers (prepared in Reference Preparation Examples 1, 2 and 3) were caused to react with maleic anhydride without using catalyst to synthesize succinic acid derivatives.

After the reaction, unreacted starting materials of butene oligomer and maleic anhydride and by-products were removed by distillation and silica chromatography treatment. As a result, the succinic acid derivative having the unsaturated olefin moiety as represented by the following formula [6] or formula [7] could be obtained. The properties of succinic acid derivatives are shown in Table 2.

TABLE 2

Properties of Succinic Acid Derivatives

| Reference Prep. Example | Fed Butene Oligomer | Mn (*3) | Mw/Mn | Yield Ratio of Formula [6]/[7] (*4) (% by mole) |
|---|---|---|---|---|
| 4 | Ref. Prep. Ex. 1 | 210 | 1.0 | 80/20 |
| 5 | Ref. Ex. Prep. 2 | 662 | 1.4 | 81/19 |
| 6 | Ref. Ex. Prep. 3 | 2400 | 1.5 | 80/20 |

(*3): Reference Preparation Example 4 was measured by MS. Reference Preparation Examples 5 and 6 were measured by GPC and expressed in terms of polystyrene.
(*4): Ratio of integrated values of peaks of the respective olefin moieties in the structures of the formulae [6] and [7] measured by $^{13}$C-NMR.

<Structural Determination of Highly Reactive Butene Oligomer and Succinic Acid Derivative>

Concerning the highly reactive butene oligomer (the following structural formula [A]) and succinic acid derivatives (the following structural formulae [B] and [C]) that were prepared through the above process, the following chemical analyses were carried out to identify the respective chemical structures.

The structural formula [A] herein represents the butene oligomer having the terminal vinylidene group as represented by the above formula [5]. The structural formulae [B] and [C] represent the succinic acid derivatives having the terminal structures as represented by the above formulae [6] and [7], respectively. The substance as represented by the structural formula [C] contains cis/trans geometrical isomers.

The determination of terminal group structures was carried out with infrared spectrophotometry (IR) and nuclear magnetic resonance (NMR) of one-dimension and two-dimension. The regularity of isobutene skeleton in the molecules of derivatives was confirmed by the above HSQC method and INADEQUATE method using NMR.

As samples for measurement, Reference Preparation Example 2 was used as a highly reactive butene oligomer and Reference Preparation Example 5, as a succinic acid derivative.

The results of analysis on these samples are shown in Tables 3 to 5.

In Tables 3 and 4, the symbols of ① to ⑩ and ⓐ to ⓒ added to the peaks of spectrum data indicate the symbols affixed to the constituent carbons in each structural formula. In order to show the details more clearly, the data are roughly classified into three parts in a butene oligomer, namely, terminal group, starting group and main chain of polybutene.

Figure 2:
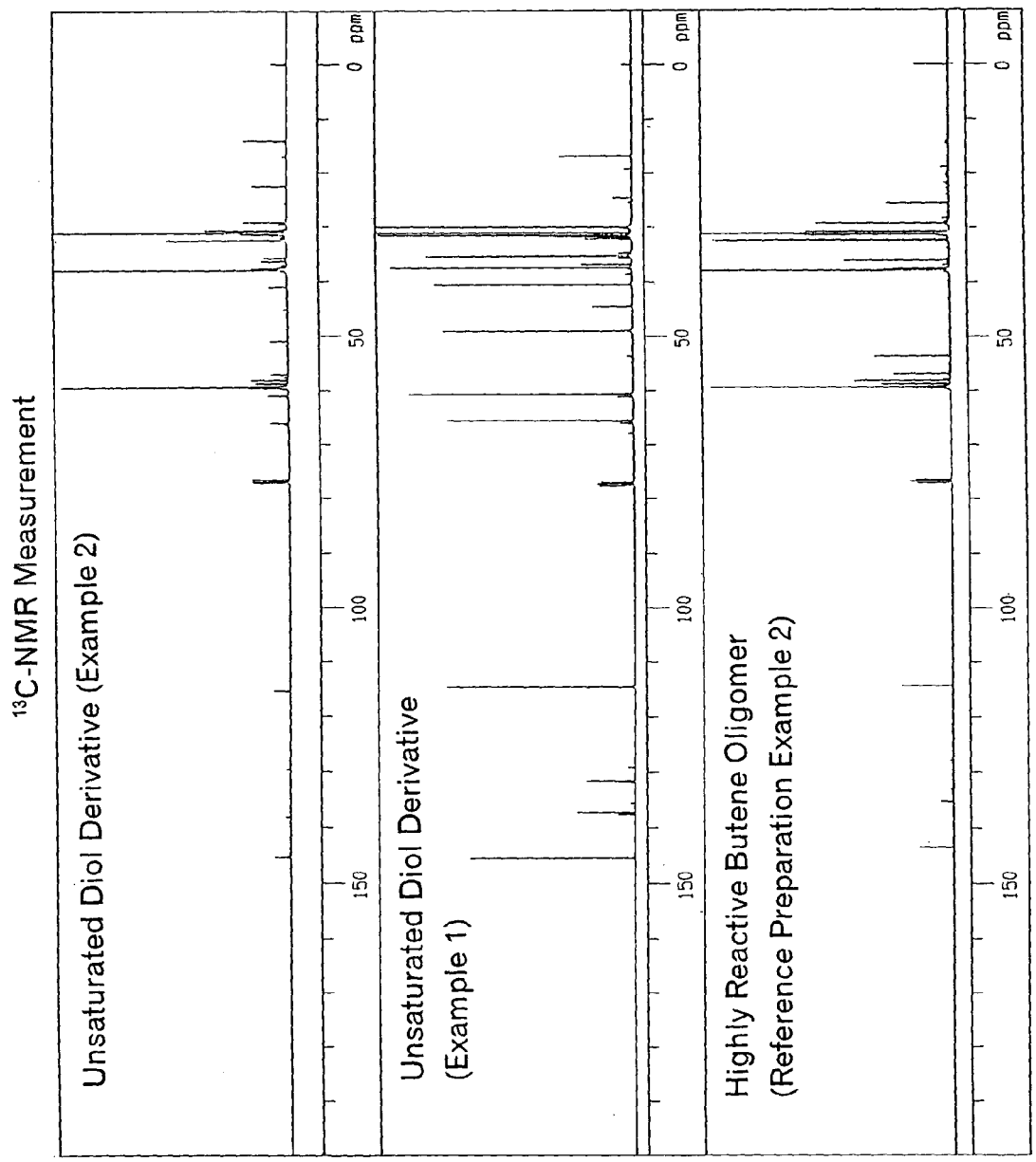
FIG. 2 shows charts of $^{13}$C-NMR measurement concerning the same samples as the above ones.
Figure 3:
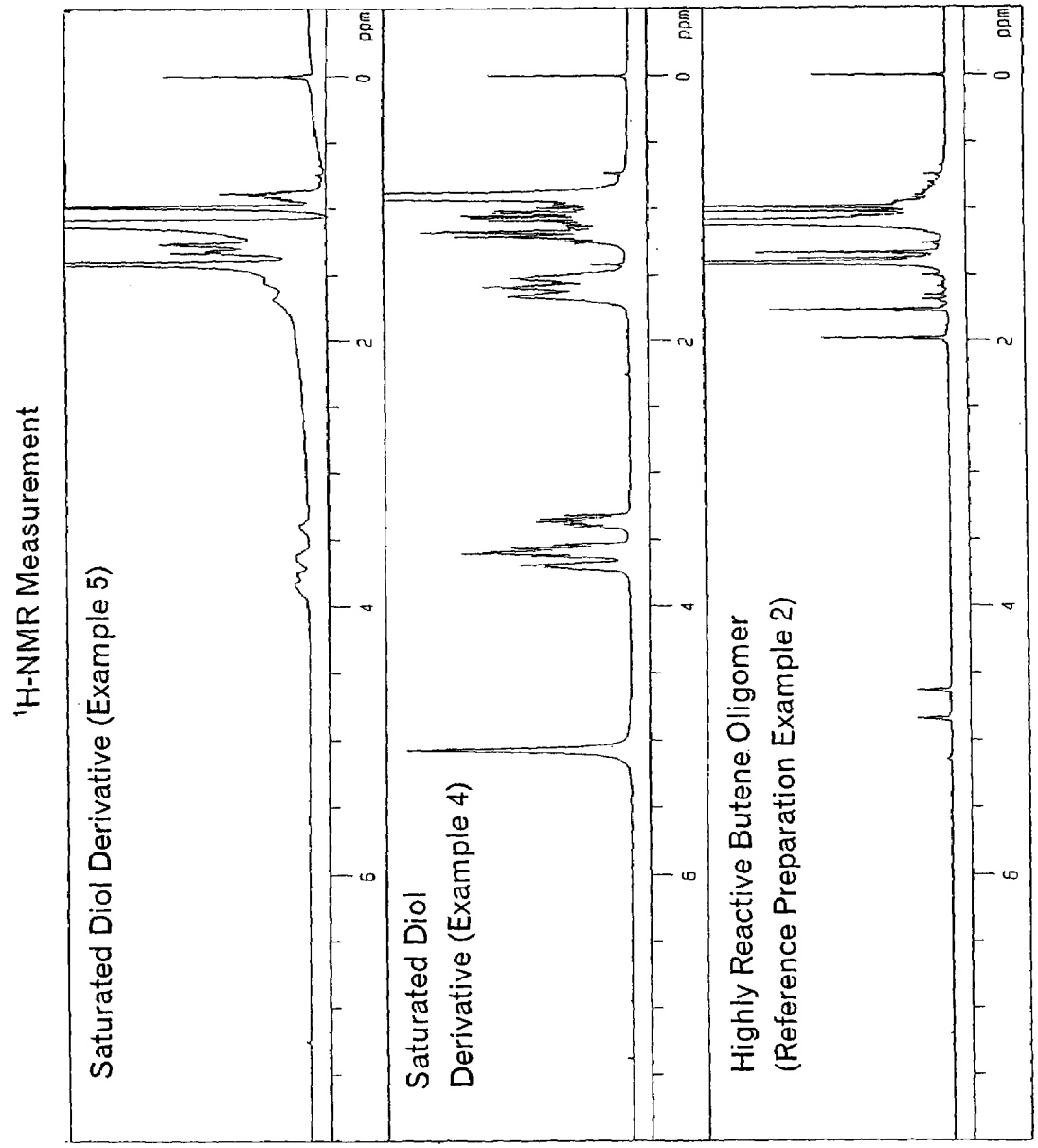
FIG. 3 shows charts of $^1$H-NMR measurement on the saturated diol derivatives and a starting material of highly reactive butene oligomer.
Figure 4:
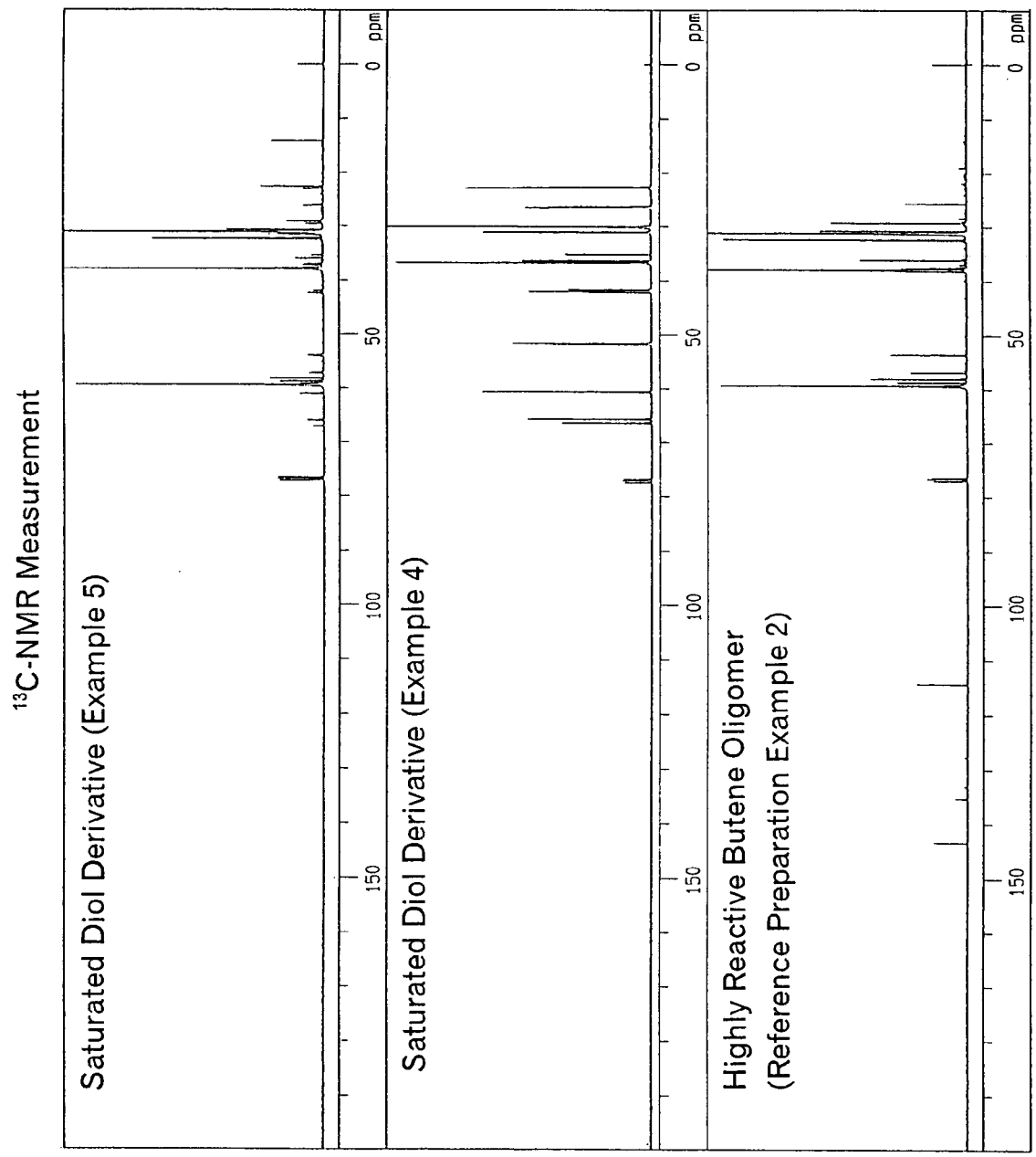
FIG. 4 shows charts of $^{13}$C-NMR measurement concerning the same samples as the above ones.

Charts of $^1$H-NMR measured on highly reactive butene oligomers (Reference Preparation Example 2) are shown in FIGS. 1 and 3. Charts of $^{13}$C-NMR measured on the same sample as the above are shown in FIGS. 2 and 4. Furthermore, in each of FIGS. 5 and 6, the charts of FT-IR measured on the same sample are shown.

TABLE 5

Wave Number of Absorption by FT-IR

| Structural Formula | Characteristic Absorption (cm$^{-1}$) |
|---|---|
| [A] | 2952, 2960, 1633, 892 |
| [B] | 2952, 2960, 1863, 1782, 1633, 892 |
| [C] | 2952, 2960, 1863, 1782, 1633 |

Each optical rotation (Na-D (589.3 nm)) of succinic acid derivatives of the structural formulae [B] and [C] was 0.000 degree.

EXAMPLES 1 TO 3

<Preparation of Unsaturated Diol Derivatives>

As a preparation apparatus, a four-neck flask of 1 liter in internal volume was set in a heating medium bath of constant temperature. The apparatus was equipped with a nitrogen-introducing pipe, a adjustable stirrer, a reaction temperature indicator, an inlet port for dropping feed material, and a refluxing device.

In the first place, a predetermined amount of LiAlH$_4$ (Table 6) was dispersed and dissolved in anhydrous THF in

TABLE 3

Chemical Shift in $^1$H-NMR Measurement
[399.65 MHz, CDCl$_3$, Internal Standard: TMS]
Symbols in parentheses indicate splitting patterns.
(s: singlet, d: doublet, t: triplet, br: broad)

| Structural Formula | Terminal Group | | | | | | Starting Group | | Main Chain of Formula [1] | |
|---|---|---|---|---|---|---|---|---|---|---|
| | ①-H | ②-H | ⑤-H | ⑥-H | ⑦-H | ⑧-H | ⓐ-H | ⓒ-H | CH$_3$ | CH$_2$ |
| [A] | 1.1 (s) | 2.0 (s) | 4.8 (d) | 1.8 (s) | — | — | 1.0 (s) | unclear | 1.1 (br) | 1.4 (br) |
| [B] | 0.9 (s) | 1.9 (s) | 2.3 (t) | 4.9 (d) | unclear | unclear | 1.0 (s) | unclear | 1.1 (br) | 1.4 (br) |
| [C] | 1.1 (s) | 5.3 (s) | unclear | 0.9 (s) | unclear | unclear | 1.0 (s) | unclear | 1.1 (br) | 1.4 (br) |
| Geometrical Isomer of [C] | — | 5.4 (s) | — | — | — | — | — | — | — | — |

TABLE 4

Chemical Shift by $^{13}$C-NMR
[100.40 MHz, CDCl$_3$, Internal Standard: TMS]

| Structural Formula | Terminating Group | | | | | | | | | | Starting Group | | | Main Chain of Formula [1] | | |
|---|---|---|---|---|---|---|---|---|---|---|---|---|---|---|---|---|
| | ①-C | ②-C | ③-C | ④-C | ⑤-C | ⑥-C | ⑦-C | ⑧-C | ⑨-C | ⑩-C | ⓐ-C | ⓑ-C | ⓒ-C | CH$_3$ | Quaternary Carbon | CH$_2$ |
| [A] | 30.6 | unclear | 53.7 | 144 | 114 | 29.1 | — | — | — | — | 32.5 | 35.8 | 56.7 | 31.2 | 38.1 | 59.5 |
| [B] | 29.8 | 31.6 | 48.8 | 143 | 38.9 | 116 | 39.2 | 33.8 | 170.4 | 174.0 | 32.5 | 35.8 | 56.7 | 31.2 | 38.1 | 59.5 |
| [C] | 30.8 | unclear | 140 | 128 | 42.8 | 16.4 | 39.1 | 32.9 | 170.6 | 174.1 | 32.5 | 35.8 | 56.7 | 31.2 | 38.1 | 59.5 |
| Geometrical Isomer of [C] | — | — | 141 | 129 | — | — | — | — | — | — | — | — | — | — | — | — | the flask. Subsequently, the predetermined amount of succinic acid derivative (Table 6) diluted previously with a reaction solvent of anhydrous THF was added dropwise into the liquid dispersion through the inlet port, while the temperature of THF reflux was maintained.

After dropping, reaction was carried out for two hours with maintaining the refluxing temperature of THF. After the reaction, the reacted solution was cooled to 0° C. with ice, then pure water was slowly added dropwise with carefully observing the generation of heat in order to deactivate the unreacted $LiAlH_4$ in the reaction system. After confirming the complete deactivation of $LiAlH_4$, the liquid organic layer was diluted with a large amount of n-hexane, and it was followed by neutralization and water washing using saturated saline solution and water.

The organic layer obtained by the neutralization and water washing, was dried with anhydrous sodium sulfate. Then the solution was concentrated by distillation. As a result, the intended unsaturated diol compounds could be obtained almost quantitatively in the respective examples. The properties of the obtained unsaturated diol compounds are shown in Table 7.

TABLE 6

Conditions for Synthesizing Unsaturated Diol Derivatives

| | Feed of Succinic Acid Derivative | | | |
|---|---|---|---|---|
| | Kind of Feed (Molecular | Fed Qty. | | Feed Qty. of $LiAlH_4$ |
| Example | Weight: Mn) | g | mole | g | mole |
| 1 | Ref. Prep. Ex. 4 (210) | 10.5 | 0.05 | 9.5 | 0.25 |
| 2 | Ref. Prep. Ex. 5 (662) | 33.1 | 0.05 | 9.5 | 0.25 |
| 3 | Ref. Prep. Ex. 6 (2400) | 120.0 | 0.05 | 9.5 | 0.25 |

Reaction conditions of Examples 1 to 3:
Refluxing temperature of THF × 2 hours

TABLE 7

Results of Synthesis of Unsaturated Diol Derivatives

| | | Properties of Unsaturated Diol Derivatives | | |
|---|---|---|---|---|
| Example | Yield of Synthesis (*5) (%) | Mn (*6) | Mw/Mn | Yield Ratio of Formulae [D]/[E] (*7) (% by mole) |
| 1 | 99.0 | 200 | 1.0 | 80/20 |
| 2 | 98.5 | 651 | 1.4 | 81/19 |
| 3 | 98.6 | 2382 | 1.5 | 80/20 |

(*5): Yield relative to the feed of succinic acid derivative.
(*6): Example 1 was measured by MS. Examples 2 and 3 were measured by GPC and expressed in terms of polystyrene.
(*7): Ratio of integrated values of peaks of olefins in the structures of the following formulae [D] and [E] measured by $^{13}$C-NMR.

<Determination of Structure of Unsaturated Diol Derivatives>

In order to determine chemical structures of unsaturated diol derivatives of the following structural formulae [D] and [E], the same method as used in determining the structures of succinic acid derivatives, was employed.

The structural formula [D] represents the unsaturated diol obtained from the succinic acid derivative of the foregoing formula [B]. The structural formula [E] represents the diol obtained from the succinic acid derivative of the formula [C]. The substance of the structural formula [E] contains cis/trans isomers.

[D]

$$HC_3 - \overset{\textcircled{b}}{\underset{CH_3}{\overset{\textcircled{a}CH_3}{\underset{|}{C}}}} - \left[ CH_2 - \overset{\textcircled{1}CH_3}{\underset{CH_3}{\overset{\textcircled{2}}{\underset{|}{C}}}} \right]_n - CH_2 - \overset{\textcircled{4}}{\underset{\textcircled{6}CH_2}{\overset{\textcircled{5}}{\underset{|}{C}}}} - CH_2 - \overset{\textcircled{7}}{\underset{\textcircled{9}CH_2}{\overset{\textcircled{8}}{\underset{|}{C}H}}} - \overset{\textcircled{8}}{\underset{\textcircled{10}CH_2}{CH_2}}$$

$$\text{OH} \quad \text{OH}$$

[E]

$$HC_3 - \overset{\textcircled{b}}{\underset{CH_3}{\overset{\textcircled{a}CH_3}{\underset{|}{C}}}} - \left[ CH_2 - \overset{\textcircled{1}CH_3}{\underset{CH_3}{\overset{\textcircled{2}}{\underset{|}{C}}}} \right]_n - CH = \overset{\textcircled{4}}{\underset{\textcircled{6}CH_3}{\overset{\textcircled{5}}{\underset{|}{C}}}} - CH_2 - \overset{\textcircled{7}}{\underset{\textcircled{9}CH_2}{\overset{\textcircled{8}}{\underset{|}{C}H}}} - \overset{\textcircled{8}}{\underset{\textcircled{10}CH_2}{CH_2}}$$

$$\text{OH} \quad \text{OH}$$

In FIG. 1, the carts of $^1$H-NMR measured on unsaturated diol derivatives of Examples 1 and 2 are shown. In FIG. 2 are shown the charts of $^{13}$C-NMR measured on the same samples as the above. For the purpose of comparison, the result of highly reactive butene oligomer (Reference Preparation Example 2) is also shown in each figure.

The results of analysis in these measurement are shown in Tables 8 and 9.

TABLE 8

Chemical Shift by $^1$H-NMR
[399.65 MHz, $CDCl_3$, Internal Standard: TMS]
The symbols in parentheses indicate splitting patterns.
(s: singlet, d: doublet, br: broad)

| Structural Formula | Terminal Group | | | | | | | Starting Group | | Main Chain of Formula [1] | |
|---|---|---|---|---|---|---|---|---|---|---|---|
| | ①-H | ③-H | ⑤-H | ⑥-H | ⑦-H | ⑧-H | ⑨ or ⑩-H | —OH | ⓐ-H | ⓒ-H | $CH_3$ | $CH_2$ |
| [D] Example 1 | — | 1.9 (s) | 1.8–2.2 | 4.8 (d) | 1.8–1.9 | 1.5–1.7 | 3.3–3.8 | 4.8 | 0.9 (s) | — | — | — |

TABLE 8-continued

Chemical Shift by ¹H-NMR
[399.65 MHz, CDCl₃, Internal Standard: TMS]
The symbols in parentheses indicate splitting patterns.
(s: singlet, d: doublet, br: broad)

| Structural Formula | Terminal Group | | | | | | | | Starting Group | | Main Chain of Formula [1] | |
|---|---|---|---|---|---|---|---|---|---|---|---|---|
| | ①-H | ③-H | ⑤-H | ⑥-H | ⑦-H | ⑧-H | ⑨ or ⑩-H | —OH | ⓐ-H | ⓒ-H | $CH_3$ | $CH_2$ |
| [D] Example 2 | 0.9 (s) | 2.0 (s) | 1.8–2.2 | 4.8 (d) | 1.8–1.9 | 1.7–1.9 | 3.3–3.7 | 3.8 | 1.0 (s) | unclear | 1.1 (br) | 1.4 (br) |
| [E] Example 1 | — | 5.2 (s) | unclear | 0.9 (s) | unclear | unclear | unclear | 4.8 | 1.1 (s) | — | — | — |
| Geom. Isomer of the above | — | 5.3 (s) | — | — | — | — | — | — | — | — | — | — |
| [E] Example 2 | 1.1 (s) | 5.2 (s) | unclear | 0.9 (s) | unclear | unclear | unclear | 3.8 | 1.0 (s) | unclear | 1.1 (br) | 1.4 (br) |
| Geom. Isomer of the above | — | 5.3 (s) | — | — | — | — | — | — | — | — | — | — |

TABLE 9

Chemical Shift by ¹³C-NMR
[100.40 MHz, CDCl₃, Internal Standard: TMS]

| Structural Formula | Terminal Group | | | | | | | | | | Starting Group | | | Main Chain of Formula [1] | | |
|---|---|---|---|---|---|---|---|---|---|---|---|---|---|---|---|---|
| | ①-C | ②-C | ③-C | ④-C | ⑤-C | ⑥-C | ⑦-C | ⑧-C | ⑨-C | ⑩-C | ⓐ-C | ⓑ-C | ⓒ-C | $CH_3$ | Quaternary Carbon | $CH_2$ |
| [D] Example 1 | — | — | 49.1 | 146 | 40.6 | 115 | 37.6 | 5.6 | 65.6 | 60.8 | 30.0 | 31.7 | — | — | — | — |
| [D] Example 2 | 29.2 | unclear | 51.0 | 145 | 41.1 | 115 | 37.7 | 36.3 | 66.1 | 61.0 | 32.5 | 35.7 | 57.0 | 31.2 | 38.1 | 59.5 |
| [E] Example 1 | — | — | 137.4 | 131.8 | 44.7 | 16.9 | 37.1 | unclear | 66.0 | 60.9 | 31.0 | unclear | — | — | — | — |
| Geom. Isomer of the above | — | — | 137.8 | 131.6 | — | — | — | — | — | — | — | — | — | — | — | — |
| [E] Example 2 | 29.2 | unclear | 138.2 | 129.6 | 45.2 | 17.0 | unclear | unclear | 66.4 | 61.0 | 32.5 | 35.8 | 56.7 | 31.2 | 38.1 | 59.5 |
| Geom. Isomer of the above | — | — | 138.4 | 129.4 | — | — | — | — | — | — | — | — | — | — | — | — |

Figure 5:
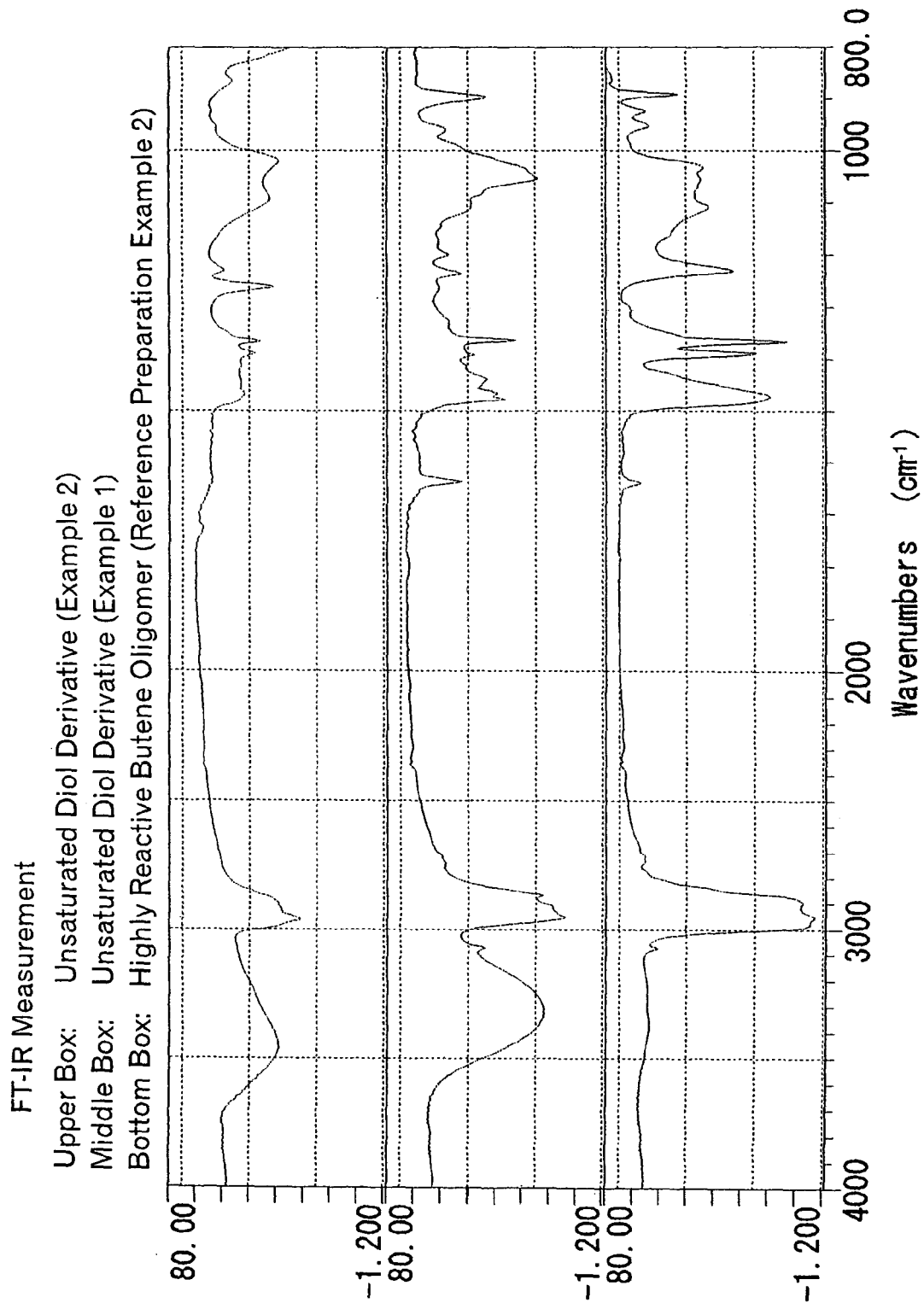
FIG. 5 shows charts of FT-IR measurement concerning the samples as those in the above FIGS. 1 and 2.

In FIG. 5, the charts of FT-IR measured on unsaturated diol derivatives of Examples 1 and 2 are shown. For the purpose of comparison, the result of highly reactive butene oligomer (Reference Preparation Example 2) is also shown.

The data of characteristic absorption based on these measurements are shown in Table 10.

TABLE 10

Measurement by FT-IR

| Structural Formula | Characteristic Absorption (cm⁻¹) |
|---|---|
| [D] Example 1, 2 | 3324, 2952, 2960, 1633, 892 |
| [E] Example 1, 2 | 3324, 2952, 2960, 1633 |

Each optical rotation (Na-D (589.3 nm)) of unsaturated diol derivatives of the structural formulae [D] and [E] was 0.000 degree.

From the above data of NMR and IR, it was confirmed that the terminal succinic acid group disappeared and a new unsaturated diol terminal group appeared in the starting succinic acid derivative. Furthermore, from the data of NMR, it was understood that the isobutylene skeleton of the formula [1] constitutes 80% or more of growing chains of oligomer. In addition, the chemical structures of unsaturated diol derivatives of the present invention could be determined, which have the terminal groups of the formulae [3] and [4].

As being understood in view of the chemical structure of the above unsaturated diol derivative, the carbon marked with ⑦ can be asymmetric. However, the derivatives produced in the present examples were optically inactive, with which it was confirmed that they are racemic mixtures.

EXAMPLES 4 TO 6

<Preparation of Saturated 1,4-Butanediol Derivative>

As a preparation apparatus, an autoclave of 100 ml in internal volume was installed in a thermally controllable heating medium bath. The apparatus was provided with inlet ports for introducing nitrogen gas and hydrogen gas, an outlet for sampling, a pressure indicator, a reaction temperature indicator, a controllable stirrer, and a refluxing device.

In the first place, each predetermined amount of unsaturated diol derivatives produced in the Examples 1 to 3 (Table 11) was dissolved in n-hexane. Subsequently, the predetermined amount of 10% Pd-C hydrogenation catalyst (Table 11) was added into each solution without preliminary reducing treatment.

After that, nitrogen displacement was carried out sufficiently, and the autoclave was pressurized with hydrogen gas to attain the pressure of 1.0 MPa. Then, the reaction was carried out for 3 hours while the temperature of the solution was maintained at 60° C. After the reaction, the reaction solution was taken out, the hydrogenating catalysts of solid powder was filtered off under reduced pressure, and the organic layer in the filtrate was concentrated by distillation. As a result, the saturated diol compound could be obtained almost quantitatively (Table 12).

TABLE 11

Conditions for Synthesizing Saturated Diol Derivative

| | Feed of Unsaturated Diol Derivative | | Charge of |
| --- | --- | --- | --- |
| Example | Kind of Feed (Molecular Weight: Mn) | Feed Qty. g / mole | Pd—C (parts by weight) (*8) |
| 4 | Product of Exam. 1 (200) | 5.0 / 0.025 | 10 |
| 5 | Product of Exam. 2 (651) | 16.3 / 0.025 | 10 |
| 6 | Product of Exam. 3 (2382) | 59.6 / 0.025 | 10 |

Reaction Conditions in Examples 4 to 6: Hydrogen Pressure 1.0 MPa, 60° C. × 3 hours
(*8): Parts by weight relative to unsaturated diol derivative as fed

TABLE 12

Results of Synthesis of Saturated Diol Derivative

| | Yield of Synthesis (*9) | Properties of Saturated Diol Derivative | |
| --- | --- | --- | --- |
| Example | (%) | Mn (*10) | Mw/Mn |
| 4 | 99.5 | 202 | 1.0 |
| 5 | 99.8 | 650 | 1.4 |
| 6 | 99.4 | 2385 | 1.5 |

(*9): Yield relative to succinic acid derivative as fed.
(*10): Example 4 was measured by MS. Examples 5 and 6 were measured by GPC and expressed in terms of polystyrene.

<Structural Determination of Saturated Diol Derivative>

In order to determine the chemical structure of saturated diol derivative of following structural formula [F], the same method as that used in determining the structures of the succinic acid derivatives, was employed.

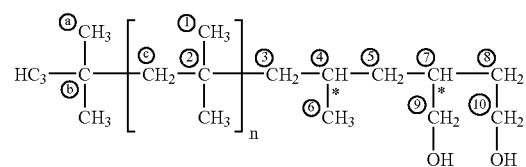

[F]

In FIG. 3, the charts of $^1$H-NMR measured on saturated diol derivatives of Examples 4 and 5 are shown. In FIG. 4 are shown the charts of $^{13}$C-NMR measured on the same samples. For the purpose of comparison, the result of highly reactive butene oligomer of Reference Preparation Example 2) is also shown in each figure.

The results of analysis based on these measurements are shown in Tables 13 and 14.

TABLE 13

Chemical Shift by $^1$H-NMR
[399.65 MHz, CDCl$_3$, Internal Standard: TMS]
Symbols in parentheses indicate splitting patterns. (s: singlet, m: multiplet, br: broad)

| Structural Formula | Terminal Group | | | | | | Starting Group | | Main Chain of Formula [1] | |
| --- | --- | --- | --- | --- | --- | --- | --- | --- | --- | --- |
| | ①-H | ③ or ⑤ -H | ⑥-H | ⑦ or ⑧ -H | ⑨-H | ⑩-H | —OH | ⓐ-H | ⓒ-H | CH$_3$ / CH$_2$ |
| [F] Example 4 | — | 1.0–1.2 | 0.9 (m) | 1.4–1.8 | 3.3–3.6 | 3.5–3.8 | 5.1 | 0.9 (s) | — | — / — |
| [F] Example 5 | 0.9 (s) | 1.2–1.4 | 0.9 (m) | 1.5–1.8 | 3.3–3.6 | 3.6–3.8 | 3.8 | 1.0 (s) | unclear | 1.1 (br) / 1.4 (br) |

TABLE 14

Chemical Shift by $^{13}$C-NMR
[100.40 MHz, CDCl$_3$, Internal Standard: TMS]

| Structural Formula | Terminal Group | | | | | | | | | | Starting Group | | | Main Chain of Formula [1] | | |
| --- | --- | --- | --- | --- | --- | --- | --- | --- | --- | --- | --- | --- | --- | --- | --- | --- |
| | ①-C | ②-C | ③-C | ④-C | ⑤-C | ⑥-C | ⑦-C | ⑧-C | ⑨-C | ⑩-C | ⓐ-C | ⓑ-C | ⓒ-C | CH$_3$ | Quaternary Carbon | CH$_2$ |
| [F] Example 4 | — | — | 51.6 | 26.6 | 42.0 | 22.9 | 36.8 | 35.2 | 65.7 | 60.6 | 30.1 | 31.0 | — | — | — | — |

TABLE 14-continued

Chemical Shift by $^{13}$C-NMR
[100.40 MHz, CDCl$_3$, Internal Standard: TMS]

| Structural Formula | Terminal Group | | | | | | | | | | Starting Group | | | | Main Chain of Formula [1] | |
|---|---|---|---|---|---|---|---|---|---|---|---|---|---|---|---|---|
| | ①-C | ②-C | ③-C | ④-C | ⑤-C | ⑥-C | ⑦-C | ⑧-C | ⑨-C | ⑩-C | ⓐ-C | ⓑ-C | ⓒ-C | CH$_3$ | Quaternary Carbon | CH$_2$ |
| Opt. Isomer of the above | — | — | 51.8 | 26.4 | 41.7 | 22.5 | 36.8 | 36.4 | 66.4 | 60.6 | 30.2 | 31.1 | — | — | — | — |
| [F] Example 5 | 29.2 | 32.4 | 53.9 | 26.2 | 42.4 | 23.1 | 37.2 | 36.1 | 66.0 | 61.0 | 32.5 | 35.8 | 56.7 | 31.2 | 38.1 | 59.5 |
| Opt. Isomer of the above | 29.2 | 32.5 | 54.1 | 26.0 | 41.9 | 22.7 | 37.3 | 35.4 | 67.1 | 61.0 | 32.5 | 35.8 | 56.7 | 31.2 | 38.1 | 59.5 |

Figure 6:
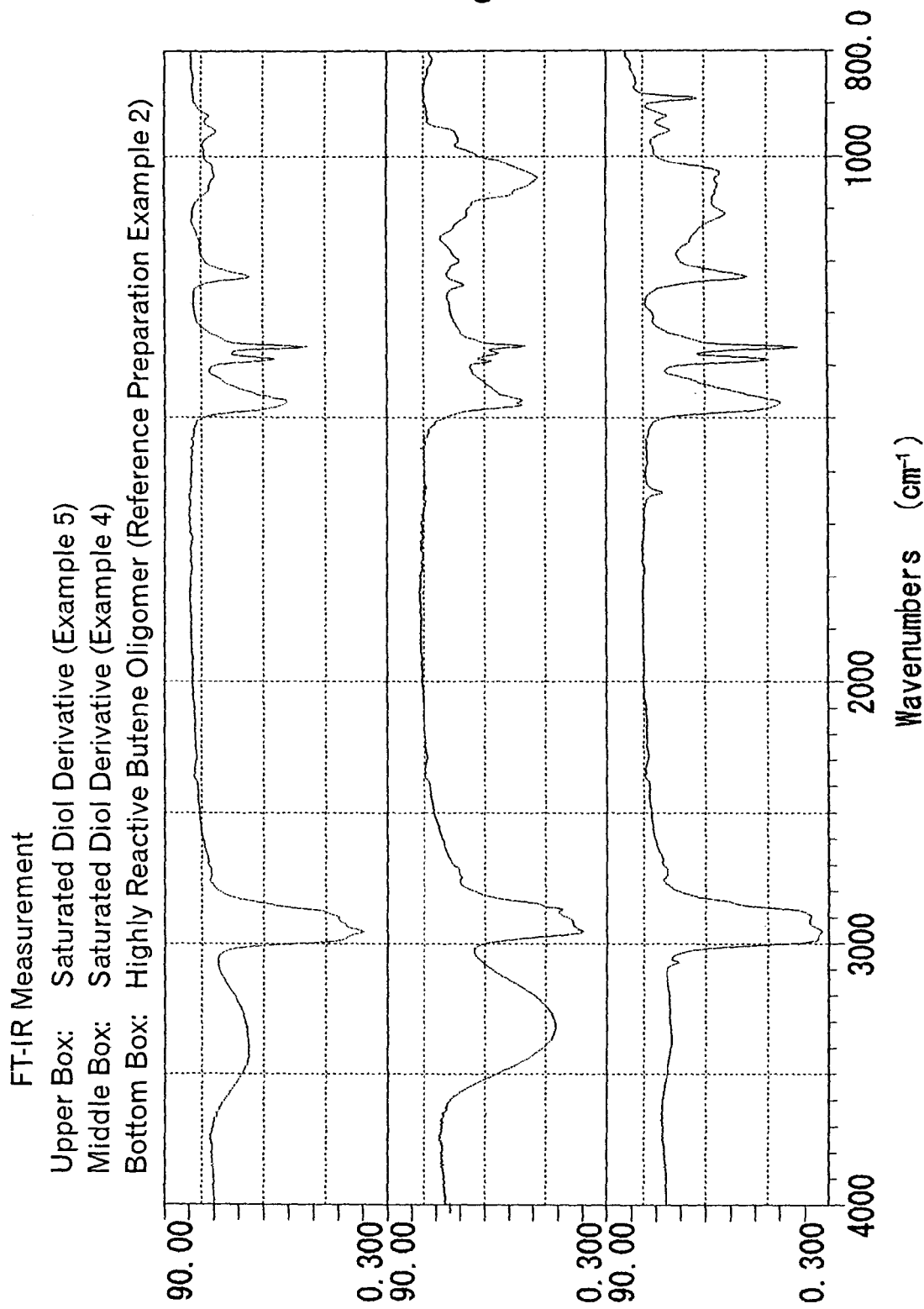
FIG. 6 shows charts of FT-IR measurement concerning the samples as those in the above FIGS. 3 and 4.

In FIG. 6, FT-IR charts measured on saturated diol derivatives of Examples 4 and 5 are shown. For the purpose of comparison, the result of highly reactive butene oligomer (Reference Example for Production 2) is also shown.

The data of characteristic absorption based on the measurement are shown in Table 15.

TABLE 15

Wave Number of Absorption by FT-IR

| Structural Formula | Characteristic Absorption (cm$^{-1}$) |
|---|---|
| [F] Examples 4, 5 | 3324, 2952, 2960 |

The optical rotation (Na-D (589.3 nm)) of the saturated diol derivative as represented by the structural formula [F] was 0.000 degree.

From the above data of NMR and IR, it was confirmed that diol groups were maintained and olefinic double bonds disappeared in unsaturated diol derivative as feed material. Furthermore, from the data of NMR, it was understood that the isobutylene skeleton as represented by the formula [1] constitutes 80% or more of growing chains of oligomer. In addition, the chemical structures of saturated diol derivatives of the present invention could be specified, which have the terminal groups as represented by the formula [2].

As being understood from the chemical structure of the above saturated diol derivative, the carbons marked with ④ and ⑦ can be asymmetric. However, the derivatives produced in the present examples were optically inactive, by which it is confirmed that they are racemic mixtures. That is, as understood also from the results of $^{13}$C-NMR measurement, they are racemic mixtures comprising 4 kinds of optical isomers, (R, R), (R, S), (S, R) and (S, S).

INDUSTRIAL APPLICABILITY

According to the present invention, it is possible to provide a butene oligomer derivative containing saturated alkyl or unsaturated olefin and having a functional group of 1,4-butanediol. Furthermore, the butene oligomer derivative of the present invention can be used as a macromonomer in synthesizing a new polymer by polycondensation or polyaddition, as a plasticizer for various kinds of plastics, as a third component capable of hardening sulfur-curable rubbers and so forth.

What is claimed is:

1. A butene oligomer derivative having the following structural conditions (1) to (3):
   (1) a terminal group on one side of a molecule is a tert-butyl group,
   (2) 80% by mole or more of the repeating structural unit of a hydrocarbon main chain are represented by the following formula [1], and
   (3) 60% by mole or more of terminal groups on the other side of said molecule are represented by the following formula [2],

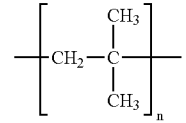
[1]

wherein n is an integer of 0 or more

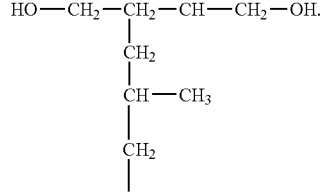
[2]

2. A butane oligomer derivative having the following structural conditions (1) to (3):
   (1) a terminal group on one side of a molecule is a tert-butyl group,
   (2) 80% by mole or more of the repeating structural units of a hydrocarbon main chain are represented by the following formula [1], and
   (3) 60% by mole or more of terminal groups on the other side of said molecule are represented by the following formula [3] or [4],

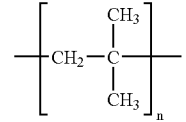
[1]

wherein n is an integer of 0 or more

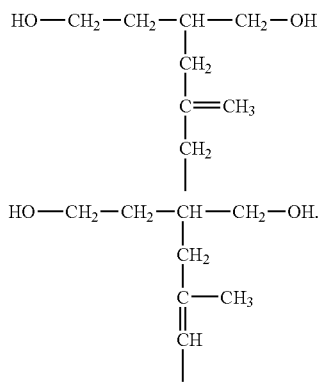

3. A derivative in accordance with claim 1 wherein n is at least 5.

4. A derivative in accordance with claim 3 wherein n is at least 16.

5. A derivative in accordance with claim 4 wherein n is no greater than 200.

6. A derivative in accordance with claim 2 wherein n is at least 5.

7. A derivative in accordance with claim 6 wherein n is at least 16.

8. A derivative in accordance with claim 7 wherein n is no greater than 200.

* * * * *